United States Patent [19]

Klaveness

[11] Patent Number: 4,760,173
[45] Date of Patent: Jul. 26, 1988

[54] NMR CONTRAST AGENTS

[75] Inventor: Jo Klaveness, Oslo, Norway

[73] Assignee: Nycomed AS, Norway

[21] Appl. No.: 102,533

[22] Filed: Sep. 29, 1987

Related U.S. Application Data

[62] Division of Ser. No. 739,228, May 30, 1985, Pat. No. 4,714,607.

[30] Foreign Application Priority Data

May 30, 1984 [GB] United Kingdom ............... 8413772

[51] Int. Cl.$^4$ .................................. C07C 101/447
[52] U.S. Cl. ........................................ 562/449
[58] Field of Search ........................ 562/449, 450

[56] References Cited

U.S. PATENT DOCUMENTS

| 4,318,898 | 3/1982 | Molter et al. | 562/450 |
| 4,418,208 | 11/1983 | Nunn et al. | 562/450 |
| 4,612,185 | 9/1986 | Dean | 562/450 |

OTHER PUBLICATIONS

Loberg et al., "Development of New Radiopharmaceuticals . . .", *Radiochemistry and Radiopharmaceuticals*, 17,7,633–638.

Nunn et al., "A Structure-Distribution-Relationship Approach . . .", J. Nucl. Med., 24: 423–430, 1983.

*Primary Examiner*—James H. Reamer
*Attorney, Agent, or Firm*—Bacon & Thomas

[57] ABSTRACT

There are provided NMR contrast agents comprising water-soluble paramagnetic metal chelates, preferably of Cr(III), Fe(III) or Gd(III), wherein the chelating entity is an anilide group containing organic moiety, preferably a compound of formula I

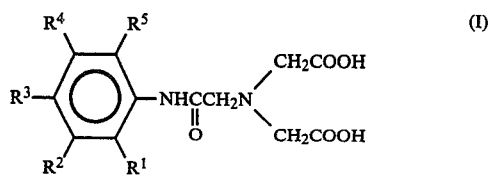

(I)

wherein $R^1$ to $R^5$ may represent hydrogen or halogen atoms, optionally halogenated alkyl or alkoxy groups or carboxyl groups. The agents are especially suitable for use in NMR imaging of the hepatobiliary system.

1 Claim, No Drawings

NMR CONTRAST AGENTS

This application is a division of application Ser. No. 739,228 filed May 30, 1985 now U.S. Pat. No. 4,714,608.

The present invention relates to certain paramagnetic anilide-based chelates and their use as contrast agents in NMR imaging.

It has long been known that paramagnetic materials can be used to reduce the spin relaxation times in NMR spectroscopy. Recently, with the development of NMR imaging, an imaging technique particularly suitable for diagnostic application, the use of paramagnetic materials as NMR contrast agents has been proposed. Thus since the contrast in the NMR image is dependent strongly on the variation in relaxation times across the sample being imaged, the introduction of a material, such as a paramagnetic compound into a localised portion of the sample being imaged, e.g. into a particular body organ, will increase the contrast between that portion and the sample as a whole in the NMR image generated.

Paramagnetic compounds have been used in experimental NMR imaging for some years. Both soluble and insoluble paramagnetic compounds have been described in the literature although here we will only review the use of water-soluble compounds.

Compounds that exhibit paramagnetic properties are compounds which have unpaired electrons. The Table below shows some examples of paramagnetic compounds.

TABLE

| Paramagnetic substances | |
| --- | --- |
| Paramagnetic metal ions | |
| Transition metals | $Co^{2+}$, $Mn^{2+}$, $Cu^{2+}$, $Cr^{3+}$, $Fe^{2+}$, $Fe^{3+}$ |
| Lanthanides | $Eu^{3+}$, $Gd^{3+}$, $Dy^{3+}$, $Ho^{3+}$ |
| Paramagnetic chelates* | MnEDTA, GdEDTA, MnDTPA, CoEDTA, CrDTPA, FeNTA |
| Stable free radicals | nitroxides |
| Molecules with unpaired electrons | $O_2$, NO, $NO_2$ |

*NTA = Nitrilo triacetic acid
EDTA = Ethylene diamine tetraacetic acid
DTPA = Diethylene triamine pentaacetic acid Molecular oxygen has been used as a vascular paramagnetic contrast agent, but molecules such as NO and $NO_2$ are too toxic to be used in NMR imaging. Nitroxides however have been proposed as renal NMR contrast agents by Brasch et al in Radiology 147 (1983) 773.

Paramagnetic metals and chelates are now the most frequently used contrast agents in experimental NMR imaging. Manganese chloride ($MnCl_2$) has been used as an NMR contrast agent in animal studies, but the salt is probably too toxic for use in in vivo human experiments. Other paramagnetic ions such as $Gd^{3+}$, $Dy^{3+}$, $Ho^{3+}$, $Fe^{3+}$ and $Cr^{3+}$ have also been used in in vitro or in in vivo NMR experiments.

Schering AG in EP-A-71564 describe the preparation and use in NMR imaging of salts of paramagnetic chelates such as MnEDTA, DyEDTA, HoEDTA, and GdDTPA. Stable EDTA and DTPA chelates are excreted in the urine and thus are potential parenteral NMR contrast agents for the enhancement of renal structures.

Paramagnetic chelates with desferrioxamine B, glucoheptonic acid and inositol hexaphosphoric acid have also been used as renal contrast agents in NMR imaging. A selective decrease in relaxation times of infarcted myocardium with the use of manganese-labelled monoclonal antibody has been shown.

Various particulate paramagnetic compounds have been studied for reticuloendothelial enhancement in NMR imaging of the liver, the particulate material being trapped in the reticuloendothelial system. We are unaware however that as yet any soluble paramagnetic chelates have been described as a parenterally administrable NMR contrast agent concentrating in the the liver or the bile.

We have now found that certain soluble anilidebased paramagnetic chelates can be administered orally or parenterally, e.g. by intravenous injection, to achieve a contrast effect in NMR imaging, e.g. of the liver and the bile.

In one aspect, the invention thus provides an NMR contrast agent comprising at least one water-soluble paramagnetic metal chelate together with at least one physiologically acceptable carrier or excipient, wherein the chelating entity is an anilide group containing organic moiety, more particularly, an anilide derivative of an imino polyacetic acid (i.e. a compound having at least three N-attached acetic acid residues one of which is converted into an anilide derivative while at least two remain as free acid groups).

The chelates in the contrast agent of the invention preferably have high lipophilicity and particularly preferably are complexes of a paramagnetic metal, e.g. a paramagnetic lanthanide or transition metal, with a chelating agent of formula I

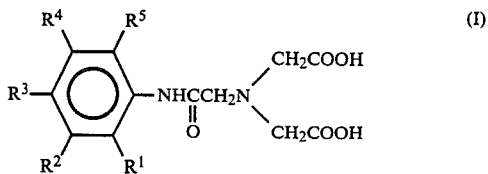

(wherein $R^1$ to $R^5$, which may be the same or different, each represent hydrogen or halogen atoms, optionally halogenated alkyl or alkoxy groups or carboxyl groups) or physiologically acceptable salts thereof.

In the chelating entity, $R^1$ to $R^5$ are conveniently optionally halogenated lower ($C_{1-4}$) alkyl or alkoxy groups but preferably are hydrogen, fluorine, lower (i.e. $C_1$-$C_4$) alkyl, or fluorinated lower alkyl (e.g. $CF_3$). Particularly preferably $R^1$ to $R^5$ are fluorine, or $R^1$, $R^3$ and $R^5$ are hydrogen and $R^2$ and $R^4$ are -$CF_3$, or $R^1$ and $R^5$ are lower alkyl and $R^2$ to $R^4$ are hydrogen.

We have found that the contrast agents of the invention are particularly effective as hepatobiliary contrast agents when the paramagnetic metal in the chelate is a trivalent cation, especially preferably $Cr^{3+}$, $Fe^{3+}$ or $Gd^{3+}$.

The chelates of the non-radioactive paramagnetic metals with compounds of formula I or salts thereof are novel and thus in a further aspect the invention provides a water-soluble paramagnetic chelate, for example of chromium or gadolinium, wherein the chelating entity is the residue of a compound of formula I or a physiologically acceptable salt thereof.

The chromium (III) chelate of N-(2,6-diethylphenylcarbamoylmethyl) iminodiacetic acid and its salts are particularly preferred.

Certain chelating agents of formula I are known and their chelates with $^{99m}Tc$ have been used as cholescintigraphic agents. These "technetium chelates" are described for example by Nunn et al in J. Nucl. Med 24 (1983) 423 and Loberg et al in J. Nucl. Med. 17 (1976) 633 and are found to possess low renal secretion, high hepatobiliary specificity and rapid hepatocellular transit times.

Certain of the chelating agents of formula I however are novel and thus in another aspect the invention provides N-[3,5-bis(trifluoromethyl)phenylcarbamoylmethyl] iminodiacetic acid and the physiologically acceptable salts thereof. This novel compound may be prepared by reacting disodium iminodiacetic acid with ω-chloro-3,5-bis(trifluoromethyl) acetanilide, and its salts may be prepared in conventional ways from the free acid and a physiologically acceptable base.

In a still further aspect, the invention provides a process for the preparation of an NMR contrast agent according to the invention, which process comprises admixing in aqueous solution an anilide group containing chelating agent (e.g. a compound of formula I or physiologically acceptable salt thereof) and an at least sparingly soluble paramagnetic metal compound, e.g. a water-soluble paramagnetic metal salt the counterion whereof is physiologically acceptable or an at least sparingly soluble oxide or carbonate, optionally in suspension.

In a yet further aspect the invention provides a process for the preparation of a water-soluble non-radioactive paramagnetic chelate according to the invention, which process comprises admixing in aqueous solution a chelating agent of formula I or a physiologically acceptable salt thereof and an at least sparingly soluble paramagnetic metal compound, e.g. a water-soluble paramagnetic metal salt the counterion whereof is physiologically acceptable or an at least sparingly soluble oxide or carbonate, optionally in suspension.

Where chelate formation is by reaction of a compound of formula I with a trivalent paramagnetic ion, this is preferably achieved by reaction of one equivalent of the paramagnetic metal with two equivalents of the chelating entity.

The contrast agents of the invention may be preformed or may alternatively be prepared directly before administration by mixing in aqueous solution the chelating agent and a soluble compound containing the paramagnetic metal e.g. in salt form with a physiologically acceptable counter ion, for example a halide, such as chloride. Where the chelating entity is itself in salt form the counter ion should also be physiologically acceptable and may for example be meglumine or an alkali metal ion such as sodium. With the chelating agents of formula I, chelate formation appears to happen within a few seconds at from ambient temperature to the boiling temperature of the solution.

Thus in another aspect the invention provides a kit comprising a water-soluble paramagnetic metal compound, e.g. a $Gd^{3+}$, $Cr^{3+}$ or $Fe^{3+}$ compound, and an anilide-based chelating agent; either or both being optionally in solution in a physiologically acceptable carrier solvent, e.g. water for injections.

Where the contrast agent of the invention is supplied in the form of a solution of the paramagnetic chelate in a physiologically acceptable carrier solvent, e.g. water for injections, the solution may be in concentrated form for dilution before administration.

As it is preferred that the contrast agent of the invention be at physiological pH, it may also contain a buffer.

Administration of the contrast agents of the invention is preferably by intravenous injection of solutions containing the paramagnetic chelate in sufficient concentration to provide the desired hepatobiliary NMR-contrast effect. In this respect solutions containing the paramagnetic metal in concentrations of from 0.1 to 200 mM are suitable. Alternatively the contrast agents are formulated in forms suitable for oral administration, e.g. solutions, tablets or capsules. The contrast agents may conveniently be administered in amounts of from $10^{-4}$ to $10^{-1}$ mmol paramagnetic metal/kg bodyweight.

Thus in a still further aspect, the invention provides a method of generating an NMR image suitable for use in diagnosis which method comprises administering an NMR contrast agent of the invention to a human or animal subject and generating an NMR image of at least a part of said subject in which said contrast agent is present.

A preferred embodiment of the method of the invention comprises NMR imaging wherein hepatobiliary contrast enhancement is achieved by administering an effective amount of at least one chelate of a paramagnetic metal (preferably $Cr^{3+}$, $Fe^{3+}$ or $Gd^{3+}$) with an anilide-based chelating agent (preferably the residue of a compound of formula I or a salt thereof) intravenously to a human or animal subject and generating an NMR image of the liver and/or biliary system of said subject.

In a yet further aspect, the invention thus provides the use of a water-soluble paramagnetic metal chelate wherein the chelating entity is an anilide group containing organic moiety for the manufacture of a diagnostic agent for use in diagnosis of the human or animal body using NMR imaging.

Our experiments have shown chelates according to the invention to be efficient relaxation agents in vitro and to have high hepatobiliary specificity and rapid hepatocellular transit times. Thus in a rabbit, after intravenous injection of 0.0075 mmol gadolinium/kg bodyweight in the form of a chelate with a compound of formula I in which the phenyl moiety is a 2,6-dimethylphenyl group, the contrast enhancement of the liver and the intestine 15 minutes after injection was very good. At this time the contrast agent had started to excrete from the liver. The chelate did not, however, show any contrast enhancement of the kidneys.

The rabbit was killed 1 hour after the injection, and the relaxation times in the liver and the kidneys were measured. The relaxation times in these organs were normal, which shows that all of the chelates had left the liver during the first hour. The quality of the NMR picture obtained with this chelate was much better than the general standard of NMR pictures published in the literature.

The contrast agents and chelates of the invention will now be illustrated further by the following non-limiting Examples:

Intermediate 1

N-(2,6-dimethylphenylcarbamoylmethyl)iminodiacetic acid

The title compound was prepared from ω-chloro2,6-dimethylacetanilide and iminodiacetic acid by the procedure described by Callery et al. in J. Med. Chem. 19 (1976) 962. The product was isolated in 75% yield following reflux of the mixture for 3 hours; m.p. 216°–217° C.

Intermediate 2

N-(2,6-diethylphenylcarbamoylmethyl)iminodiacetic acid

The title compound was prepared from ω-chloro2,6-diethylacetanilide and iminodiacetic acid in a manner analogous to the preparation of Intermediate 1. The mixture was refluxed for 5 hours; yield 75% m.p. 187°–188° C.

Intermediate 3

N-(2,4,6-trimethylphenylcarbamoylmethyl)iminodiacetic acid

The title compound was prepared from ω-chloro2,4,6-trimethylacetanilide and iminodiacetic acid in a manner analogous to the preparation of Intermediate 1. The mixture was refluxed for 4½ hours; yield 79%; m.p. 220°–221° C.

Intermediate 4

N-(2,3,4,5,6-pentafluorophenylcarbamoylmethyl)iminodiacetic acid

The title compound was prepared from ω-chloro2,3,4,5,6-pentafluoroacetanilide and iminodiacetic acid in a manner analogous to the preparation of Intermediate 1. The mixture was refluxed for 1 hour; yield: 78%; m.p. 182°–183° C.

EXAMPLE 1

N-[3,5-Bis(trifluoromethyl)phenylcarbamoylmethyl] iminodiacetic acid

Chloroacetyl chloride (17.8 g=157.5 mmol) was added dropwise to a solution of 3,5-bis(trifluoromethyl)aniline (34.4 g=150 mmol) and triethylamine (15.2 g=150 mmol) in toluene (300 ml) under cooling on ice. The temperature was slowly adjusted to ambient temperature and the reaction mixture was stirred for 1½ hours. Toluene was removed by distillation and the oily residue was washed with $H_2O$ (300 ml). The oily residue was suspended in $H_2O$ (300 ml) and placed in the refrigerator overnight. The precipitate was isolated by filtration and dissolved in boiling n-hexane (400 ml). The solution was filtered and cooled to ambient temperature. The crystals of ω-chloro-3,5-bis(trifluoromethyl)acetanilide were isolated by filtration. Yield 80%; m.p. 87°–88° C.

Disodium iminodiacetic acid (37.2 g=210 mmol) and ω-chloro-3,5-bis(trifluoromethyl)acetanilide (30.6 g=100 mmol) were dissolved in a solution of ethanol-water (50:50) at 80° C. After 5 hours the ethanol was removed by distillation and the residue was extracted with diethylether (3×60 ml). The ether was removed by distillation and the pH was adjusted to 2. The precipitate was filtered off and washed with dilute HCl (200 ml), dissolved in boiling ethanol (400 ml) and precipitated with $H_2O$ (750 ml). The title compound was isolated by filtration. Yield 22.2 g (55%); m.p. 201° C. $^1$H-NMR(DMSO-d$_6$): δ3.77 (s;—CH$_2$—), 7.72 and 8.37 (Ph), 11.20 (s; COOH), 11.54 (broad s, —NH—). $^{13}$C-NMR(DMSO-d$_6$): δ56.0 (—CH$_2$—), 59.1 (—CH$_2$—), 105.3- 141.6 (Ph and -CF$_3$)

Calculated (for $C_{14}H_{12}F_6N_2O_5$): C 41.80, H 3.01, N 6.96, F 28.34. Found: C 41.87, H 3.23, N 7.30, F 28.2.

General procedure for formation of a gadolinium (III)-, iron (III)- and chromium (III) chelate with Intermediates 1 to 4 and Example 1

An aqueous solution of the disodium salt of the chelating agent (1 equivalent) and the metal (III) chloride hexahydrate (2 equivalents) was stirred and refluxed for one hour. The stirring was continued for one hour at ambient temperature. The pH was adjusted to 1.5 with dilute HCl and the metal chelate was isolated by filtration.

General procedure for formation of a manganese (II)-, copper (II), cobalt (II)-, and nickel (II) chelate with Intermediates 1 to 4 and Example 1

An aqueous solution of the disodium salt of the chelating agent (1 equivalent) and the hydrated metal (II) choride (1 equivalent) was stirred and heated to boiling. After cooling to ambient temperature the stirring was continued for one hour. The metal chelate was isolated by filtration.

EXAMPLE 2

Gadolinium (III) chelate of N-(2,6-dimethylphenylcarbamoylmethyl) iminodiacetic acid The gadolinium (III) chelate was isolated from a 0.15M solution as white crystals Yield: 72.2%, M.p. >350° C. Solubility as sodium salt in water: >0.02M.

Analysis: $C_{28}H_{32}N_4O_{10}GdNa$. Calculated: C 43.96, H 4.21, N 7.32, Gd 20.56, Na 2.73; Found: C 43.76, H 4.38, N 7.16, Gd 20.30, Na 2.70.

Specific relaxation rate enhancement (SRRE) was measured in a NMR proton spin analyzer (RADX Corp., Houston, Tex., USA) at 10 MHz in glycerol: water 1:2 (v:v) at 37° C.: 5.22 s$^{-1}$ mM$^{-1}$.

EXAMPLE 3

Gadolinium (III) chelate of N-(2,6-diethylphenylcarbamoylmethyl) iminodiacetic acid The gadolinium (III) chelate was isolated from a 0.15M solution as white crystals. Yield: 63%. M.p.: >350° C. Solubility as sodium salt in water: >0.1M.

EXAMPLE 4

Gadolinium (III) chelate of N-(2,4,6-trimethylphenylcarbamoylmethyl) iminodiacetic acid The gadolinium (III) chelate was isolated from a 0.15M solution as white crystals. Yield: 66%. M.p.: >350° C. Solubility as sodium salt in water: >0.1M.

EXAMPLE 5

Gadolinium (III) chelate of N-(2,3,4,5,6-pentafluorophenylcarbamoylmethyl)i iminodiacetic acid The gadolinium (III) chelate was isolated from a 0.15M solution as white crystals. Yield: 43%. M.p.: >350° C. Solubility as sodium salt in water: >0.1M.

EXAMPLE 6

Gadolinium (III) chelate of N-[3,5-bis(trifluoromethyl)phenylcarbamoylmethyl] iminodiacetic acid The gadolinium (III) chelate was isolated from a 0.15M solution as white crystals. Yield: 79%. M.p.: >350° C. Solubility as sodium salt in water: >0.1M.

EXAMPLE 7

Iron(III) chelate of N-(2,6-dimethylphenylcarbamoylmethyl)iminodiacetic acid

The iron(III) chelate was isolated as light yellow powder. Yield: 85%. M.p.: 220° C. (decomp.). Analysis: $C_{28}H_{33}N_4O_{10}Fe$ Calculated: C 52.43, H 5.19, N 8.74, Fe 8.71; Found: C 51.59, H 5.23, N 8.63, Fe 8.71. SRRE: $1.86\ s^{-1}\ mM^{-1}$ Preparation of the meglumine salt of the iron(III) chelate of N-(2,6-dimethylphenylcarbamoylmethyl) iminodiacetic acid The iron(III) chelate of N-(2,6-dimethylphenylcarbamoylmethyl) iminodiacetic acid (160 mg=0.25 mmol) was dissolved in methanol (20 ml) and N-methylglucamine (49 mg=0.25 mmol) was added over a period of 15 minutes. The solution was evaporated to dryness and the meglumine salt of the iron(III) chelate of N-(2,6- dimethylphenylcarbamoylmethyl) iminodiacetic acid was isolated as yellow crystals in a quantitative yield.

EXAMPLE 8

Iron(III) chelate of N-(2,6-diethylphenylcarbamoylmethyl) iminodiacetic acid

The iron(III) chelate was isolated from a 0.14M solution as a light yellow powder. Yield: 63%, M.p.: 250° C. (decomp.)

EXAMPLE 9

Iron(III) chelate of N-(2,4,6-trimethylphenylcarbamoylmethyl) iminodiacetic acid The iron(III) chelate was isolated from a 0.04M solution as light yellow powder Yield: 88%. M.p.: 200° C. (decomp.)

EXAMPLE 10

Iron(III) chelate of N-[3,5-bis(trifluoromethyl)phenylcarbamoyl-methyl)] iminodiacetic acid The iron(III) chelate was isolated from a 0.04M solution as light yellow powder. Yield: 78%. M.p.: 200° C. (decomp.).

EXAMPLE 11

Chromium(III) chelate of N-(2,6-dimethylphenylcarbamoylmethyl) iminodiacetic acid The chromium(III) chelate was isolated from a 0.03M solution as grey powder. Yield: 68%. M.p.: >320° C.

The meglumine salt of the complex was prepared in the same way as described in Example 12 (A). Analysis: $C_{35}H_{50}N_5O_{15}Cr$ Calculated: C 50.48, H 6.05, N 8.41, Cr 6.24; Found: C 50.68, H 5.82, N 7.83, Cr 6.81.

EXAMPLE 12

Chromium(III) chelate of N-(2,6-diethylphenylcarbamoylmethyl) iminodiacetic acid and its meglumine salt The chromium(III) chelate was isolated from 0.14M solution as grey powder. Yield: 71%. M.p.: >320° C.

(A) Preparation of the meglumine salt of the chromium (III) chelate of N-(2,6-diethylphenylcarbamoylmethyl) iminodiacetic acid To a solution of the chromium(III) chelate of N-(2,6-diethylphenylcarbamoylmethyl) iminodiacetic acid (140 mg=0.2 mmol) in methanol (38 ml) was added N-methylglucamine (39 mg=0.2 mmol) over a period of 15 minutes. The solution was evaporated to dryness and the meglumine salt of the complex was isolated as a pink powder in a quantitative yield. M.p.: >320° C. Relaxation time ($T_1$) of a 10 mM solution of the product in water was 158 msec. $T_1$ (pure water): 3300 msec.

(B) Preparation of chromium(III) chelate of N-(2,6-diethylphenylcarbamoylmethyl) iminodiacetic acid and its meglumine salt N-(2,6-diethylphenylcarbamoylmethyl) iminodiacetic acid (1.29 g=4 mmol) and freshly prepared $Cr(OH)_3$ (206 mg=2 mmol) was suspended in $H_2O$ (250 ml). N-methylglucamine (390 mg=2 mmol) was added in small portions while the suspension was stirred and heated at 95° C. for 48 hours. The pink reaction mixture was filtered and evaporated to dryness. The meglumine salt of chromium(III) - N-(2,6-diethylphenylcarbamoylmethyl) iminodiacetic acid was isolated in 98% yield as pink powder.

EXAMPLE 13

Chromium(III) chelate of N-(2,4,6-trimethylphenylcarbamoylmethyl) iminodiacetic acid The chromium(III) chelate was isolated from a 0.28M solution as grey powder. Yield: 63%. M.p.: >320° C.

EXAMPLE 14

Cobalt(II) chelate of N-(2,6-dimethylphenylcarbamoylmethyl) iminodiacetic acid

The cobalt(II) chelate was isolated from a 0.2M solution as a pink powder. Yield: 59%, M.p.: >300° C. $T_1$ (10 mM; $H_2O$): 698 msec.

EXAMPLE 15

Cobalt(II) chelate of N-(2,6-diethylphenylcarbamoylmethyl) iminodiacetic acid

The cobalt(II) chelate was isolated from a 0.27M solution as a pink powder. Yield: 90%. M.p.: >300° C. Analysis: $C_{16}H_{20}N_2O_5Co$ Calculated: C 50.67, H 5.31, N 7.39, Co 15.54; Found: C 50.70, H 5.54, N 7.00, Co 14.90.

EXAMPLE 16

Cobalt(II) chelate of N-(2,4,6-trimethylphenylcarbamoylmethyl) iminodiacetic acid The cobalt(II) chelate was isolated from a 0.11M solution as pink powder. Yield: 86%. M.p.: >300° C.

EXAMPLE 17

Cobalt(II) chelate of
N-[3,5-bis(trifluoromethyl)phenylcarbamoylmethyl)] iminodiacetic acid The cobalt(II) chelate was isolated from a 0.18M solution as pink powder. Yield: 87%. M.p.: >300° C.

EXAMPLE 18

Copper(II) chelate of
N-(2,6-dimethylphenylcarbamoylmethyl) iminodiacetic acid

The copper(II) chelate was isolated as a light blue powder. Yield: 76%. M.p.: >270° C.(decomp.). Analysis: $C_{14}H_{16}N_2O_5Cu$ Calculated: C 47.26, H 4.53, N 7.87, Cu 17.86; Found: C 47.35, H 4.63, N 7.47, Cu 17.04.

EXAMPLE 19

Copper (II) chelate of
N-(2,6-diethylphenylcarbamoylmethyl) iminodiacetic acid

The copper(II) chelate was isolated from a 0.27M solution as a light blue powder. Yield: 63%. M.p.: 250° C. (decomp.).

EXAMPLE 20

Copper(II) chelate of
N-(2,4,6-trimethylphenylcarbamoylmethyl) iminodiacetic acid The copper(II) chelate was isolated from a 0.11M solution as a light blue powder. Yield: 62%. M.p.: 250° C. (decomp.).

EXAMPLE 21

Manganese(II) chelate of
N-(2,6-dimethylphenylcarbamoylmethyl) iminodiacetic acid The manganese(II) chelate was isolated from a 0.27M solution as a white powder. Yield: 57%. M.p.: >350° C.

EXAMPLE 22

Manganese(II) chelate of
N-(2,6-diethylphenylcarbamoylmethyl)iminodiacetic acid

The manganese(II) chelate was isolated from a 0.32M solution as a white powder. Yield: 80%. M.p.: >350° C.
Analysis: $C_{16}H_{20}N_2O_5Mn$ Calculated: C 51.21, H 5.37, N 7.46, Mn 14.64; Found: C 51.80, H 5.69, N 7.27, Mn 14.90.

EXAMPLE 23

Manganese(II) chelate of
N-(2,4,6-trimethylphenylcarbamoylmethyl) iminodiacetic acid The manganese(II) chelate was isolated from a 0.36M solution as a white powder. Yield: 62%. M.p.: >350° C.

EXAMPLE 24

Manganese(II) chelate of
N-(2,3,4,5,6-pentafluorophenylcarbamoylmethyl) iminodiacetic acid The manganese(II) chelate was isolated from a 0.24M solution as a white powder. yield: 47%. M.p.: >350° C. Analysis: $C_{12}H_7F_5N_2O_5Mn$ Calculated: C 35.23, H 1.72, N 6.85, Mn 13.4; Found: C 35.18, H 1.97, N 6.53, Mn 12.9.

EXAMPLE 25

Manganese(II) chelate of
N-[3,5-bis(trifluoromethyl)phenylcarbamoylmethyl)] iminodiacetic acid The manganese(II) chelate was isolated from a 0.18M solution as white powder. Yield: 82%. M.p.: >350° C.

EXAMPLE 26

Nickel(II) chelate of
N-(2,6-dimethylphenylcarbamoylmethyl) iminodiacetic acid

The nickel(II) chelate was isolated as a light green powder. Yield: 30%. M.p.: >300° C. $T_1$ (10 mM; $H_2O$) 311 msec.

EXAMPLE 27

Nickel(II) chelate of
N-(2,6-diethylphenylcarbamoylmethyl) iminodiacetic acid

The nickel(II) chelate was isolated from a 0.27M solution as a light green powder. Yield: 42%. M.p.: >300° C.

EXAMPLE 28

Nickel(II) chelate of
N-(2,4,6-trimethylphenylcarbamoylmethyl) iminodiacetic acid The nickel(II) chelate was isolated from a 0.11M solution as light green powder. Yield: 38%. M.p.: >300° C.

EXAMPLE 29

Nickel(II) chelate of
N-[3,5-bis(trifluoromethyl)phenylcarbamoylmethyl)] iminodiacetic acid The nickel(II) chelate was isolated from a 0.09M solution as light green powder. Yield: 87%. M.p.: >300° C.

Preparation of solutions for NMR imaging from isolated chelates

EXAMPLE 30

Manganese chelate of
N-(2,6-dimethylphenylcarbamoylmethyl) iminodiacetic acid

An autoclaved isotonic 30 mM solution of the manganese chelate of N-(2,6-dimethylcarbamoylmethyl) iminodiacetic acid in a 10 ml vial was prepared from:

| | |
|---|---|
| Chelate of Example 21 | 104 mg |
| Sodium chloride | 81 mg |
| Aqua purificata ad | 10 ml |

EXAMPLE 31

Gadolinium chelate of
N-(2,6-dimethylphenylcarbamoylmethyl) iminodiacetic acid

An autoclaved isotonic 13 mM solution of the sodium salt of the gadolinium chelate of N-(2,6-dimethylcarbamoylmethyl)iminodiacetic acid in a 10 ml vial was prepared from:

| | |
|---|---|
| chelate of Example 2 | 100 mg |
| Sodium chloride | 84 mg |
| Aqua purificata ad | 10 ml |

EXAMPLE 32

Preparation of capsules for oral use

| | |
|---|---|
| Chromium(III) chelate of n—(2,6-diethylphenyl-carbamoylmethyl) iminodiacetic acid (Example 12) | 306.4 mg |
| Amylum maydis | q.s. |

The powder was mixed and filled in capsules. (Capsule size 0). Each capsule contained 25 mg chromium.

Preparation of solutions for NMR imaging in situ:

EXAMPLE 33

Manganese chelate of N-(2,3,4,5,6-pentafluorophenylcarbamoylmethyl) iminodiacetic acid

Solution A

An autoclaved isotonic 28 mM solution of the disodium salt of N-(2,3,4,5,6-pentafluorophenylcarbamoylmethyl) iminodiacetic acid in a 20 ml vial was prepared from:

| | |
|---|---|
| n—(2,3,4,5,6-pentafluorophenyl-carbamoylmethyl)-iminodiacetic acid | 100 mg |
| Sodium hydroxide | 2 equivalents* |
| Sodium chloride | 68 mg |
| Aqua purificata ad | 10 ml |

*(i.e. 2 equivalents of the N—(2,3,4,5,6-pentafluorophenylcarbamoylmethyl)iminodiacetic acid)

Solution B

An autoclaved isotonic 25 mM solution of manganese chloride in 10 ml vial was prepared from:

| | |
|---|---|
| Manganese chloride (36.8% H$_2$O) | 50 mg |
| Sodium chloride | 69 mg |
| Aqua purificata ad | 10 ml |

The chelate was prepared by adding solution B to solution A. After mixing, the solution is ready for use.

EXAMPLE 34

Gadolinium chelate of N-(2,4,6-trimethyplphenylcarbamoylmethyl) iminodiacetic acid

Solution A

An autoclaved 60 mM isotanic solution of the disodium salt of N-(2,4,6-trimethylphenylcarbamoylmethyl) iminodiacetic acid in a 20 ml vial was prepared from:

| | |
|---|---|
| n—(2,4,6-trimethylphenylcarbamoyl-methyl)iminodiacetic acid | 228 mg |
| Sodium hydroxide | 2 equivalents |
| Sodium chloride | 36 mg |
| Aqua purificata ad | 10 ml |

Solution B

An autoclaved isotanic 25 mM solution of gadolinium chloride in a 10 ml vial was prepared from:

| | |
|---|---|
| Gadolinium chloride (35.9% H$_2$O) | 66 mg |
| Sodium chloride | 69 mg |
| Aqua purificata ad | 10 ml |

The chelate was prepared by adding solution B to solution A. After mixing, the solution is ready for use.

I claim:
1. N-[3,5-Bis(trifluoromethyl)phenlycarbamoylmethyl] iminodiacetic acid and physiologically acceptable salts thereof.

* * * * *